(12) United States Patent
Champagne et al.

(10) Patent No.: US 10,245,091 B2
(45) Date of Patent: Apr. 2, 2019

(54) DIP FUSION SPIKE SCREW

(71) Applicant: Exsomed International IP, LLC, Avarua, Rarotonga (CK)

(72) Inventors: Lloyd P. Champagne, Phoenix, AZ (US); Jozef Zoldos, Phoenix, AZ (US)

(73) Assignee: ExsoMed Holding Company, LLC, Phoenix, AZ (US)

( * ) Notice: Subject to any disclaimer, the term of this patent is extended or adjusted under 35 U.S.C. 154(b) by 185 days.

(21) Appl. No.: 14/984,145

(22) Filed: Dec. 30, 2015

(65) Prior Publication Data
US 2017/0189090 A1 Jul. 6, 2017

(51) Int. Cl.
*A61B 17/86* (2006.01)
*A61B 17/72* (2006.01)

(52) U.S. Cl.
CPC .......... *A61B 17/86* (2013.01); *A61B 17/7291* (2013.01)

(58) Field of Classification Search
CPC .... A61B 17/86; A61B 17/863; A61B 17/8635
See application file for complete search history.

(56) References Cited

U.S. PATENT DOCUMENTS

| | | | |
|---|---|---|---|
| 1,741,279 A | 12/1929 | Bowman | |
| 2,037,586 A | 4/1936 | Olson | |
| 2,210,455 A | 8/1940 | Hosking | |
| 2,217,951 A | 10/1940 | Hosking | |
| 2,229,892 A | 1/1941 | Hosking | |
| 2,242,003 A | 5/1941 | Lorenzo | |
| 3,275,055 A | 9/1966 | Gutshall | |
| 3,397,699 A | 8/1968 | Kohl | |
| 3,717,146 A | 2/1973 | Halloran | |
| 4,016,874 A | 4/1977 | Maffei | |
| 4,175,555 A * | 11/1979 | Herbert | A61B 17/863 606/304 |
| 4,380,414 A | 4/1983 | Capuano | |
| 4,463,753 A * | 8/1984 | Gustilo | A61B 17/863 411/386 |
| 4,471,777 A | 9/1984 | McCorkle | |
| 4,584,722 A | 4/1986 | Levy et al. | |

(Continued)

FOREIGN PATENT DOCUMENTS

| | | |
|---|---|---|
| CH | 643131 | 5/1984 |
| CH | 646858 | 12/1984 |

(Continued)

OTHER PUBLICATIONS

USPTO; Notice of Allowance dated Jul. 1, 2016 in U.S. Appl. No. 13/940,173.

(Continued)

*Primary Examiner* — Christopher Beccia
(74) *Attorney, Agent, or Firm* — Snell & Wilmer L.L.P.

(57) ABSTRACT

Devices and methods are disclosed for the fusion of joints (particularly finger joints or toe joints) in a bent (or angled) position. The device is not cannulated, straight and inserted into the joint in its straight configuration. The device is configured to have a thicker portion at its proximal end than at its distal end. The device is preferably inserted into a finger joint that is already bent at an angle, and the thin, distal end is configured to screw into and attach to the bone of second joint thereby fusing the first joint to the second joint.

23 Claims, 7 Drawing Sheets

(56) References Cited

U.S. PATENT DOCUMENTS

| | | |
|---|---|---|
| 4,608,965 A | 9/1986 | Anspach |
| 4,764,066 A | 8/1988 | Terrell |
| 4,781,191 A | 11/1988 | Thompson |
| 4,812,095 A | 3/1989 | Piacenti |
| 4,901,717 A | 2/1990 | Moore et al. |
| 4,909,789 A | 3/1990 | Taguchi et al. |
| 5,061,283 A | 10/1991 | Silvestrini |
| 5,234,299 A | 8/1993 | Giannuzzi |
| 5,312,255 A | 5/1994 | Bauer |
| 5,345,927 A | 9/1994 | Bonutti |
| 5,443,466 A | 8/1995 | Shah |
| 5,645,545 A | 7/1997 | Bryant |
| 5,667,510 A | 9/1997 | Combs |
| 5,690,633 A | 11/1997 | Taylor et al. |
| 5,853,413 A | 12/1998 | Carter et al. |
| 6,187,007 B1 | 2/2001 | Frigg |
| 6,221,006 B1 | 4/2001 | Dubrul et al. |
| 6,231,319 B1 | 5/2001 | Iida et al. |
| 6,231,413 B1 | 5/2001 | Tsukamoto |
| 6,306,140 B1 | 10/2001 | Siddiqui |
| 6,475,242 B1 | 11/2002 | Bramlet |
| 6,517,541 B1 | 2/2003 | Sesic |
| 6,592,623 B1 | 7/2003 | Bowlin et al. |
| 6,607,530 B1 | 8/2003 | Carl et al. |
| 6,808,526 B1 | 10/2004 | Magerl et al. |
| 7,041,106 B1 | 5/2006 | Carver et al. |
| 7,334,976 B2 | 2/2008 | Dicke |
| 7,465,135 B2 | 12/2008 | Fritsch |
| 7,507,242 B2 | 3/2009 | Triplett et al. |
| 7,708,738 B2* | 5/2010 | Fourcault .......... A61B 17/863 606/304 |
| 7,766,942 B2 | 8/2010 | Patterson |
| 7,988,724 B2 | 8/2011 | Salahieh et al. |
| 8,011,866 B2 | 9/2011 | Harris |
| 8,157,803 B1 | 4/2012 | Zirkle, Jr. |
| 8,398,687 B2 | 3/2013 | Vasta et al. |
| 8,414,648 B2 | 4/2013 | Reiley |
| 8,419,776 B2 | 4/2013 | Prandi et al. |
| 8,518,042 B2 | 8/2013 | Winsow et al. |
| 8,568,462 B2 | 10/2013 | Sixto et al. |
| 8,597,337 B2 | 12/2013 | Champagne |
| 8,608,783 B2 | 12/2013 | Graham et al. |
| 8,814,918 B2 | 8/2014 | Orbay et al. |
| 8,852,253 B2 | 10/2014 | Mafi |
| 8,864,804 B2 | 10/2014 | Champagne et al. |
| 8,888,429 B2 | 11/2014 | Pamer |
| 8,906,075 B2 | 12/2014 | Conley et al. |
| 9,017,404 B2 | 4/2015 | Champagne et al. |
| 9,046,120 B2 | 6/2015 | Phua |
| 9,175,715 B2 | 11/2015 | Babej |
| 9,265,600 B2 | 2/2016 | Niese |
| 9,480,515 B2 | 11/2016 | Champagne |
| 9,539,084 B2 | 1/2017 | Champagne |
| 10,098,680 B2 | 10/2018 | Champagne |
| 2001/0049529 A1 | 12/2001 | Cachia et al. |
| 2002/0045897 A1 | 4/2002 | Dixon et al. |
| 2002/0055747 A1 | 5/2002 | Cano et al. |
| 2002/0055749 A1 | 5/2002 | Esnouf et al. |
| 2002/0143337 A1 | 10/2002 | Orbay et al. |
| 2002/0198527 A1 | 12/2002 | Muckter |
| 2003/0014077 A1 | 1/2003 | Leung |
| 2003/0083661 A1 | 5/2003 | Orbay et al. |
| 2003/0130735 A1 | 7/2003 | Rogalski |
| 2004/0193217 A1 | 9/2004 | Lubbers |
| 2004/0210227 A1 | 10/2004 | Trail et al. |
| 2004/0260288 A1 | 12/2004 | Means |
| 2005/0075642 A1 | 4/2005 | Felt et al. |
| 2005/0085824 A1 | 4/2005 | Castaneda |
| 2005/0107791 A1 | 5/2005 | Manderson |
| 2005/0143735 A1 | 6/2005 | Kyle |
| 2006/0129153 A1 | 6/2006 | Klaue et al. |
| 2006/0149249 A1 | 7/2006 | Mathoulin et al. |
| 2006/0165506 A1 | 7/2006 | Panasik |
| 2006/0195099 A1* | 8/2006 | Bottlang .......... A61B 17/863 606/67 |
| 2006/0271061 A1 | 11/2006 | Beyar |
| 2006/0276790 A1 | 12/2006 | Dawson |
| 2007/0027547 A1 | 2/2007 | Rydell et al. |
| 2007/0135816 A1 | 6/2007 | Kropf et al. |
| 2007/0282342 A1 | 12/2007 | Niederberger et al. |
| 2007/0299449 A1 | 12/2007 | Allinniemi et al. |
| 2008/0183220 A1 | 7/2008 | Glazer |
| 2008/0219801 A1 | 9/2008 | Toenjes |
| 2008/0249547 A1 | 10/2008 | Dunn |
| 2008/0249574 A1 | 10/2008 | McCombs et al. |
| 2009/0062868 A1 | 3/2009 | Casutt |
| 2009/0299369 A1 | 12/2009 | Orbay et al. |
| 2010/0106254 A1 | 4/2010 | Delsignore |
| 2010/0121136 A1 | 5/2010 | Champagne |
| 2010/0130978 A1 | 5/2010 | Orbay et al. |
| 2010/0211115 A1 | 8/2010 | Tyber et al. |
| 2010/0312286 A1 | 12/2010 | Dell'Oca |
| 2010/0324556 A1 | 12/2010 | Tyber et al. |
| 2011/0009865 A1 | 1/2011 | Orfaly |
| 2011/0130794 A1 | 6/2011 | Vaidya |
| 2012/0083847 A1 | 4/2012 | Heubner et al. |
| 2012/0136398 A1 | 5/2012 | Mobasser |
| 2012/0191140 A1 | 7/2012 | Bonutti |
| 2012/0221104 A1 | 8/2012 | Altman et al. |
| 2012/0253464 A1 | 10/2012 | Hwang et al. |
| 2012/0253465 A1 | 10/2012 | Missos |
| 2013/0012987 A1 | 1/2013 | Klein et al. |
| 2013/0053961 A1 | 2/2013 | Darwin et al. |
| 2013/0060333 A1 | 3/2013 | Gonzalez |
| 2013/0131699 A1 | 5/2013 | Jiango et al. |
| 2013/0138123 A1 | 5/2013 | Stone et al. |
| 2013/0165979 A1 | 6/2013 | Greenberg et al. |
| 2013/0190872 A1 | 7/2013 | Makower et al. |
| 2013/0197592 A1 | 8/2013 | Mafi |
| 2013/0245626 A1 | 9/2013 | Lavi et al. |
| 2013/0245700 A1 | 9/2013 | Choinski |
| 2013/0245762 A1 | 9/2013 | Van Kampen et al. |
| 2013/0261662 A1 | 10/2013 | Mayer et al. |
| 2013/0274879 A1 | 10/2013 | Champagne et al. |
| 2013/0282058 A1 | 10/2013 | ElAttrache et al. |
| 2013/0325011 A1 | 12/2013 | Cleveland et al. |
| 2014/0025124 A1 | 1/2014 | Champagne et al. |
| 2014/0067063 A1 | 3/2014 | Bonutti |
| 2014/0257349 A1 | 9/2014 | Sudekum |
| 2014/0276846 A1 | 9/2014 | Mauldin |
| 2014/0336712 A1 | 11/2014 | Strnad et al. |
| 2015/0066060 A1 | 3/2015 | Bojarski |
| 2015/0094722 A1 | 4/2015 | Champagne et al. |
| 2015/0094724 A1 | 4/2015 | Champagne et al. |
| 2015/0094777 A1 | 4/2015 | Champagne et al. |
| 2015/0173737 A1 | 6/2015 | Champagne et al. |
| 2015/0182325 A1 | 7/2015 | Champagne et al. |
| 2016/0030097 A1 | 2/2016 | Mildner |
| 2016/0256290 A1* | 9/2016 | Seavey .......... A61B 17/7291 |
| 2016/0296263 A1 | 10/2016 | Champagne et al. |
| 2016/0296264 A1 | 10/2016 | Champagne et al. |
| 2016/0338748 A1 | 11/2016 | Champagne et al. |
| 2017/0027577 A1 | 2/2017 | Kubiak et al. |
| 2017/0035553 A1 | 2/2017 | Champagne et al. |
| 2017/0049167 A1 | 2/2017 | Champagne et al. |
| 2017/0196609 A1 | 7/2017 | Champagne et al. |
| 2017/0325827 A1 | 11/2017 | Champagne et al. |
| 2018/0021124 A1 | 1/2018 | Champagne et al. |

FOREIGN PATENT DOCUMENTS

| | | |
|---|---|---|
| DE | 2713386 | 11/1978 |
| DE | 102007003645 | 7/2008 |
| DE | 202013101135 | 6/2014 |
| EP | 0597223 | 5/1994 |
| EP | 1378205 | 1/2004 |
| EP | 2606843 | 6/2013 |
| EP | 602013043888.9 | 9/2018 |
| GB | 2007099 | 5/1979 |
| GB | 2181356 | 4/1987 |
| WO | WO199733537 | 9/1997 |
| WO | WO2004093700 | 4/2004 |
| WO | WO2005092226 | 10/2005 |
| WO | WO2006105935 | 12/2006 |

(56) References Cited

FOREIGN PATENT DOCUMENTS

| WO | WO2007081601 | 7/2007 |
| --- | --- | --- |
| WO | WO2007109140 | 9/2007 |
| WO | WO2008063165 | 5/2008 |
| WO | WO2010151589 | 12/2010 |
| WO | 2012050424 | 4/2012 |
| WO | WO2014011933 | 1/2014 |
| WO | 2014089522 | 6/2014 |
| WO | 2015050900 | 4/2015 |
| WO | WO2015050895 | 9/2015 |
| WO | WO2015050896 | 9/2015 |
| WO | WO2015050898 | 9/2015 |
| WO | WO2015050902 | 9/2015 |
| WO | 2016186847 | 11/2016 |

OTHER PUBLICATIONS

USPTO; Notice of Allowance dated Sep. 1, 2016 in U.S. Appl. No. 14/640,657.
USPTO; Non-Final Office Action dated Apr. 10, 2017 in U.S. Appl. No. 14/641,024.
USPTO; Final Office Action dated Jun. 2, 2017 in U.S. Appl. No. 14/503,157.
USPTO; Final Office Action dated Jun. 13, 2017 in U.S. Appl. No. 14/503,119.
USPTO; Final Office Action dated Aug. 31, 2017 in U.S. Appl. No. 14/503,228.
PCT; International Search Report and Written Opinion dated Sep. 17, 2010 in Application No. PCT/US2009/046662.
EP; Examination Report dated May 30, 2011 in Application No. EP 09774002.1.
USPTO; Office Action dated Oct. 4, 2011 in U.S. Appl. No. 12/372,712.
USPTO; Office Action dated Mar. 21, 2012 in U.S. Appl. No. 12/480,676.
EP; Examination Report dated May 25, 2012 in Application No. EP 09774002.1.
USPTO; Office Action dated May 29, 2012 in U.S. Appl. No. 12/372,712.
USPTO; Office Action dated Sep. 18, 2012 in U.S. Appl. No. 12/480,676.
USPTO; Office Action dated Mar. 22, 2013 in U.S. Appl. No. 12/372,712.
USPTO; Notice of Allowance dated Jul. 30, 2013 in U.S. Appl. No. 12/372,712.
PCT; International Search Report and Written Opinion dated Sep. 9, 2013 in Application No. PCT/US2013/050155.
USPTO; Office Action dated Sep. 24, 2013 in U.S. Appl. No. 12/480,676.
USPTO; Office Action dated Feb. 18, 2014 in U.S. Appl. No. 13/555,933.
USPTO; Notice of Allowance dated Jun. 25, 2014 in U.S. Appl. No. 13/555,933.
USPTO; Office Action dated Aug. 29, 2014 in U.S. Appl. No. 13/648,019.
PCT; International Search Report and Written Opinion dated Dec. 10, 2014 in Application No. PCT/US2014/058463.
PCT; International Search Report and Written Opinion dated Dec. 12, 2014 in Application No. PCT/US2014/058474.
USPTO; Notice of Allowance dated Dec. 31, 2014 in U.S. Appl. No. 13/648,019.
PCT; International Search Report and Written Opinion dated Jan. 20, 2015 in Application No. PCT/US2014/058448.
PCT; International Search Report and Written Opinion dated Feb. 9, 2015 in Application No. PCT/US2014/058441.
USPTO; Office Action dated Dec. 9, 2015 in U.S. Appl. No. 14/640,657.
USPTO; Office Action dated Sep. 22, 2015 in U.S. Appl. No. 14/503,228.
USPTO; Office Action dated Oct. 5, 2015 in U.S. Appl. No. 13/940,173.
USPTO; Final Office Action dated May 2, 2016 in U.S. Appl. No. 14/503,228.
USPTO; Final Office Action dated May 23, 2016 in U.S. Appl. No. 14/640,657.
USPTO; Final Office Action dated May 23, 2016 in U.S. Appl. No. 13/940,173.
USPTO; Non-Final Office Action dated Nov. 4, 2016 in U.S. Appl. No. 14/503,119.
USPTO; Non-Final Office Action dated Jan. 27, 2017 in U.S. Appl. No. 14/503,157.
USPTO; Non-Final Office Action dated Feb. 9, 2017 in U.S. Appl. No. 14/503,228.
USPTO; Non-Final Office Action dated Feb. 21, 2018 in U.S. Appl. No. 15/151,252.
USPTO; Non-Final Office Action dated Feb. 27, 2018 in U.S. Appl. No. 14/503,157.
USPTO; Non-Final Office Action dated Mar. 5, 2018 in U.S. Appl. No. 14/993,972.
USPTO; Non-Final Office Action dated Mar. 5, 2018 in U.S. Appl. No. 15/214,412.
PCT; International Search Report and Written Opinion dated Sep. 30, 2014 in Application No. PCT/US2014/058472.
PCT; International Search Report and Written Opinion dated May 4, 2016 in Application No. PCT/US2016/030850.
USPTO; Non-Final Office Action dated Nov. 1, 2017 in U.S. Appl. No. 15/297,698.
USPTO; Non-Final Office Action dated Nov. 28, 2017 in U.S. Appl. No. 15/189,845.
USPTO; Non-Final Office Action dated Nov. 30, 2017 in U.S. Appl. No. 15/189,829.
USPTO; Requirement for Restriction dated Nov. 30, 2017 in U.S. Appl. No. 15/214,412.
USPTO; Non-Final Office Action dated Dec. 8, 2017 in U.S. Appl. No. 15/146,824.
EP; Examination Report dated Feb. 12, 2016 in Application No. EP 13742332.3.
EP; 2nd Examination Report dated Oct. 11, 2016 in Application No. EP 13742332.3.
EP; Notice of Allowance dated Apr. 12, 2018 in Application No. EP 13742332.3.
USPTO; Non-Final Office Action dated Jun. 6, 2018 in U.S. Appl. No. 14/503,228.
USPTO; Notice of Allowance dated Jun. 15, 2018 in U.S. Appl. No. 15/189,845.
USPTO; Notice of Allowance dated Jul. 11, 2018 in U.S. Appl. No. 15/189,845.
USPTO; Final Office Action dated Jul. 20, 2018 in U.S. Appl. No. 14/993,972.
USPTO; Final Office Action dated Aug. 8, 2018 in U.S. Appl. No. 15/214,412.
USPTO; Final Office Action dated Aug. 13, 2018 in U.S. Appl. No. 15/151,252.
USPTO; Notice of Allowance dated Sep. 18, 2018 in U.S. Appl. No. 15/151,252.
USPTO; Final Office Action dated Oct. 17, 2018 in U.S. Appl. No. 15/146,824.

* cited by examiner

DIP FUSION SPIKE SCREW

FIELD OF THE INVENTION

The present invention relates to a device or method for the fusion of a joint, particularly the DIP joint of a finger, in a predetermined position.

BACKGROUND OF THE INVENTION

The palm of the hand is made up of bones called metacarpals, and a metacarpal connects each finger and thumb to the hand. Each finger and thumb is formed of bones called phalanges. The connection of the phalanges to the metacarpals is called a "knuckle" joint or metacarpophalangeal joint (MCP joint), and acts like a hinge when the fingers or thumb are bent.

In each finger, there are three phalanges that are separated by two joints called the interphalangeal joints (IP joints). The proximal IP joint (PIP joint) is the one closest to the MCP joint. The other joint closest to the end of the finger is the distal IP joint (DIP joint). The thumb just has one IP joint.

The joints are covered on the ends with articular cartilage. Damage to the joints may occur as a result of arthritis, a sprain or fracture, and wherein the damage either directly or indirectly affects the articular cartilage. Typically, the joint does not line up the same after the injury and causes unusual wear on the articular cartilage, eventually damaging the articular surface and causing pain and loss of mobility.

Typical methods of surgically treating a damaged joint include artificial joint replacement or fusion. Fusion (arthrodesis) is used to enable bones that make up a joint to grow together into one solid bone. Fusions are commonly used in the PIP or the DIP joints in the fingers because it is easier than replacing the joint and is an acceptable alternative to replacement in many cases.

Existing methods of fusion are inadequate, such as (a) K-wire fusion, (b) or inserting a screw through the tip of the finger and through the joint to be fused because the joint is typically fused straight (i.e., without a bend in it), which is not a natural position for the joint of a finger during normal use. Herbert and Acutrack screws and their variants have been used, but by using these, the joint (DIP joint) and end of the finger are fused in a straight position, which is unnatural since the joint is normally bent during use. DIP fusions with angles can be performed but the process is technically demanding, so it is rarely performed. Additionally, the ability to angle the joint is limited and the bone purchase is poor. An example of prior art screws is shown in FIG. 1.

Other techniques such as pin and tension band or cerclage wire do not adequately solve the problem of easily fusing a finger joint in a bent position.

SUMMARY OF THE INVENTION

The descriptions of this invention herein are exemplary and explanatory only and are not restrictive of the invention as claimed.

A device (or screw) for fusing a joint, particularly the DIP joint of a finger, comprises: (1) a first (or proximal) end, (2) a second (or distal) end, and (3) a middle portion between the first end includes a first threaded section and second end. The outer surface of the first end comprises a first threaded section, and the outer surface of the second end includes a second threaded section.

A preferred device according to the invention is a straight screw, that tapers to a narrow diameter and point, which permits bent DIP fusion by crossing a bent joint and being threadingly received in the phalange P3 and phalange P2 on either side of the joint. The design can fit virtually any size finger because of its taper and narrow outer diameter If the device of the invention has a sharp tip, the tip punctures dorsal cortex of P2 to firmly secure the device into phalange P2 at the distal side of the joint. Known designs have relatively thick tips that cannot accurately or effectively be inserted into phalange P2.

The device is preferably not cannulated, so it can taper to a tip, but optionally, the device can be cannulated. But, even if not cannulated, it uses cannulated insertional techniques which make it easy to place.

The middle portion of the device is thicker than the tapered second end. It bridges the space between the phalanges forming the joint and the extra thickness provides strength to resist the device from bending or breaking during use of the hand.

The first threaded section may have a different thread pitch, and different thread heights (as measured from the body of the device) than the second threaded section, or the first threaded section may have the same thread type and pitch as the second threaded section. The device may include a self-tapping feature at the distal end and a head at the proximal end adapted to receive an end of a driving tool, such as a screwdriver, Allen wrench or socket wrench.

A feature to prevent rotation may be included. This may take the form of the head of the device being triangular, and/or a series of nonsymmetrical features along the device to impede rotation or a texture added to the device. To achieve the same purpose the device may have other features or asymmetry at the head like ridges, wings, or barbs.

Features to allow radiographic visualization of the position of the device inserted into the body such as notches, markers, and/or fins may be included. Features that control the position of a device according to the invention independent of radiographic assessment, such as clocking devices added to the screwdriver tip, may be utilized. Further, a screwdriver may have external marks on the handle or body that indicate the position of the device when it is inserted into a patient.

The joint may be bent at an angle of between 1 and 25 degrees, at an angle of between 1 and 45 degrees, or at an angle of between 1 and 60 degrees. The device may be between ½" and 3" long, or between ¾" and 1 ¾" long. The device may be between 1 mm to 5 mm in diameter at its thickest point, or about 3 mm in diameter at its thickest point. For larger joints, the screw may be larger.

A preferred method of inserting a device according to the invention is to first bend the joint a predetermined angle, then use a K-wire to form the path through the phalanges P2, P3 of the joint into which the device will be positioned. A drill with a cannulated tip to receive the K-wire is then used to drill an opening where the K-wire has been positioned. The drill and K-wire are then removed, and a device according to the invention is threaded into the opening. The distal end threads into and is received in P2 and the proximal end in threadingly received in P3.

DETAILED DESCRIPTION OF PREFERRED EMBODIMENTS

A device or method according to the invention allows for the fusion of joints in the finger (particularly the DIP joint) in a bent (or angled) position, which is more natural when using the hand. For a finger joint, fusing the joint in a bent position allows for the patient to be able to better grip things after a successful procedure and fusion of a joint. In certain embodiments, a device for the fusion of small finger joints preferably allows for one or more of various angled positions, and the particular angle may differ for different joints. The device is preferably a screw for fusing together bones or a joint, and most preferably is used for fusing bones or a joint in a finger or toe.

Figure 1:
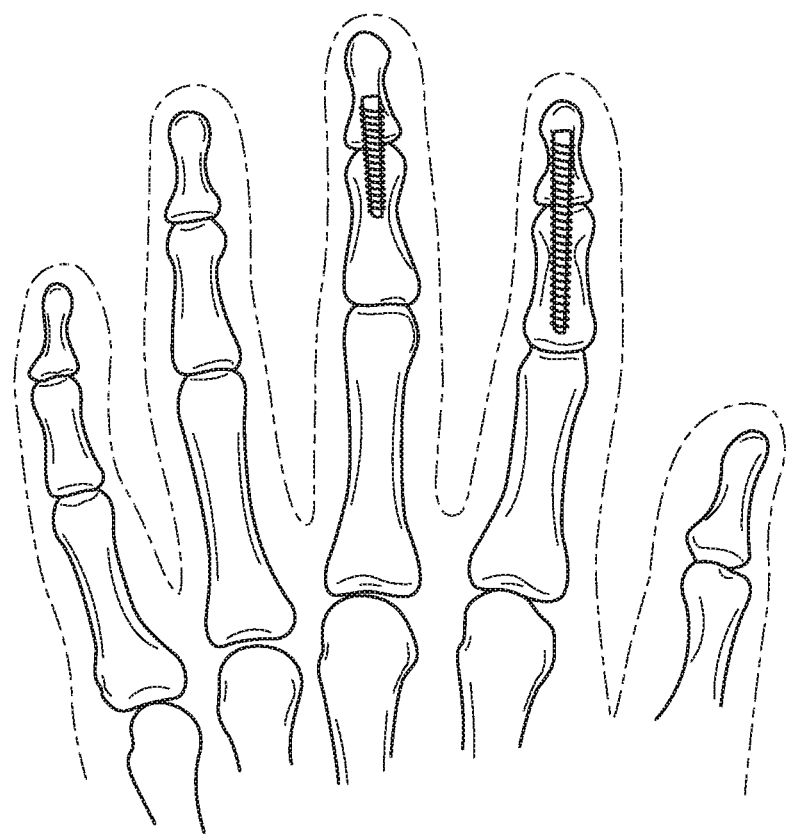
FIG. 1 depicts a prior art screw used for joint fusion.
Figure 2:
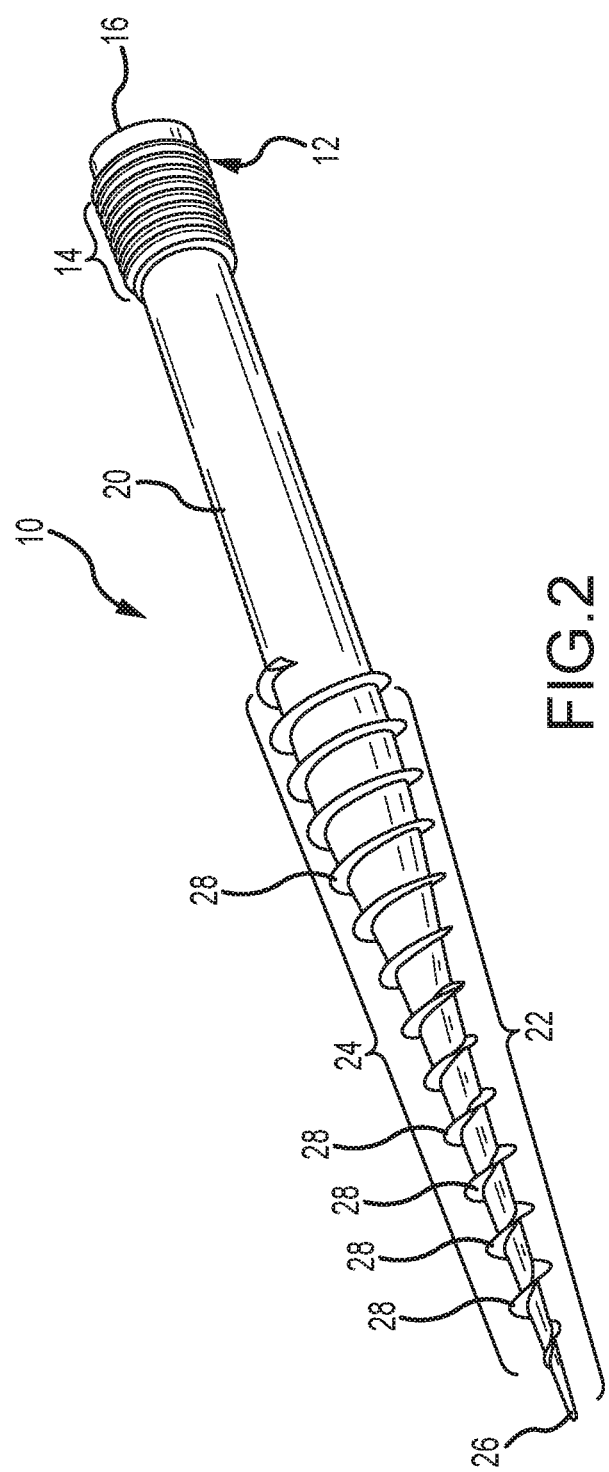
FIG. 2 is a perspective, side view of a device (or screw) according to the invention.

With reference to FIG. 2, in one embodiment, the device is a screw 10 that has a first end 12 having a first threaded portion 14, and a driver head 16. It also has a central portion 20, which is substantially cylindrical and preferably of a single diameter. It preferably has a second end 22, which has second threaded portion 24, and as shown is tapered to a tip 26. Screw 10 may have a cannula (not shown), but in this embodiment does not have one so that tip 26 is narrow and relatively sharp.

In one embodiment, end 16 is adapted to receive a Phillips head screw driver, but any suitable adaptation is possible, such as a slotted, Torx, Pozidriv, Robertson, tri-wing, Torq-Set, Spanner Head, Triple Square, or hex configuration, or any other configuration capable of pushing or screwing the device 10 into an opening, particularly one in the end of a finger DIP joint, or a toe, in order to fuse a joint. In certain embodiments, an end of the device may be adapted to be self-tapping by utilizing tip 26 and second threaded portion 24, but it is not limited thereto.

As illustrated in FIGS. 3A-6, an angle is formed in the joint before device 10 is inserted into the joint and the angle is determined according to any desired fusion position. The angle could be between about 5 and 70 degrees and most preferably between about 15 and 45 degrees.

Figure 3A:
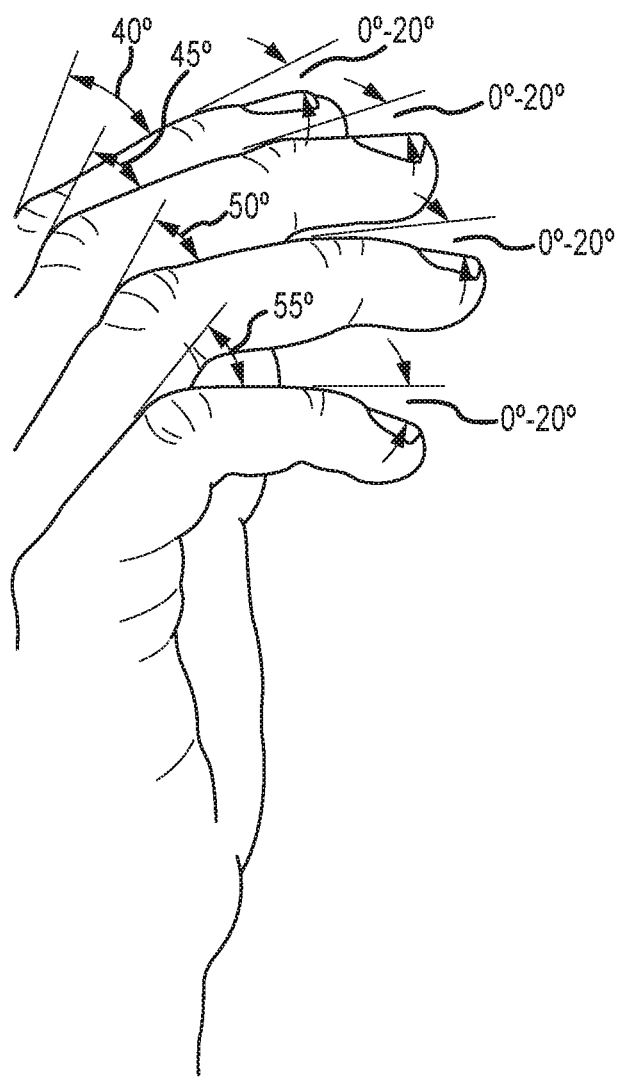
FIGS. 3A-3B show the fingers of a hand bent in a normal cascading position.
Figure 3B:
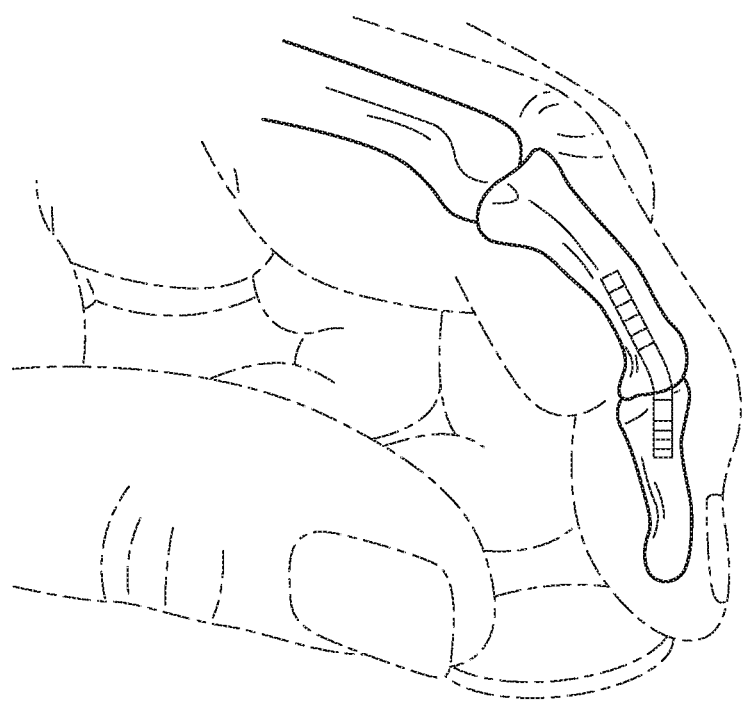
Figure 4:
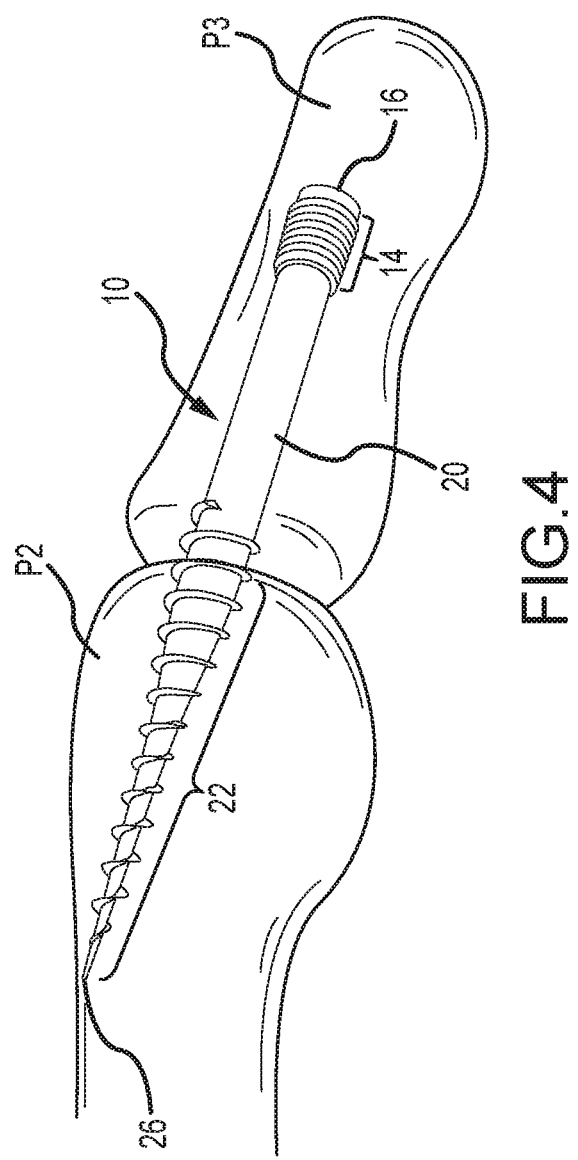
FIG. 4 shows a device according to the invention position in and fusing a DIP joint of a finger.
Figure 5:
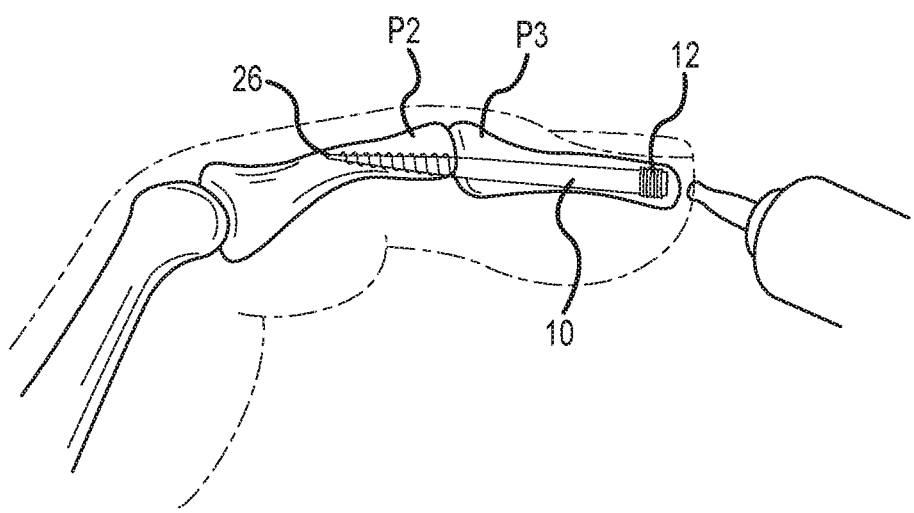
FIG. 5 shows a screw according to the present invention inserted into the DIP joint and fusing it into a bent position.
Figure 6:
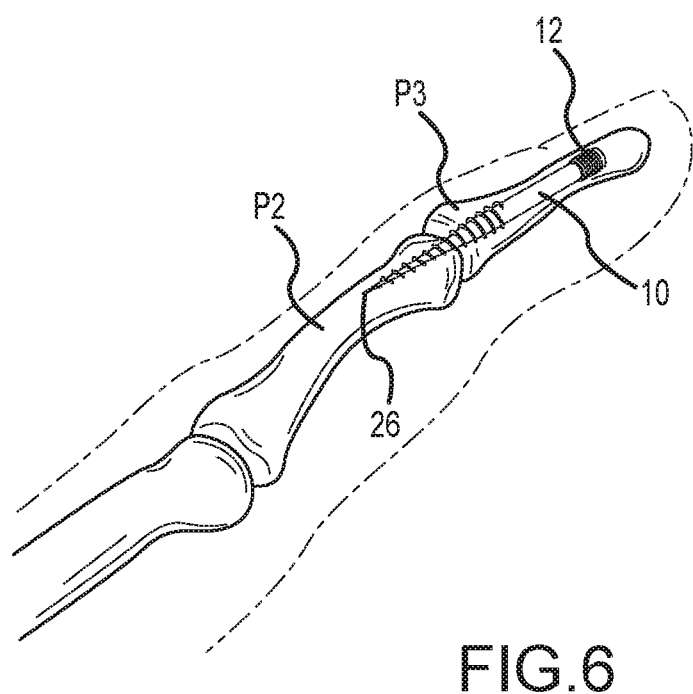
FIG. 6 shows a screw according to the present invention inserted into a DIP joint and fusing it in a relatively straight position.

FIGS. 3A-3B illustrate preferred, optimal angles for setting the different small joints in a typical hand utilizing a device according to the invention. However, different hands and different people may require different fusion angles, which can be accommodated by the invention. In some embodiments, the flexed position for the PIP joints is about 40-55 degrees, the DIP joints may vary from about 0-20 degrees, the MCP joints may vary from about 25-40 degrees, and the IP joint is typically about 20 degrees.

In some embodiments, the device material is one or more of titanium stainless steel, or plastic, but the device is not limited to these materials. The device may be comprised of any material(s) capable of fusing a finger joint, and rigid enough to prevent a patient from straightening it during ordinary use.

The length of the device, such as screw 10, depends on the size of the joint and phalanges, but is preferably between ½" and 2" and most preferably between ¾" and 1½". In many embodiments, the maximum diameter of the device is the outer diameter of the highest thread, which may be between 1 mm and 5 mm, and most preferably about 3 mm.

First threaded section 14 should be long enough and of sufficient diameter such that when inserted into a bore in a phalange, the threads grip the bone in P3 and do not allow screw 10 to twist without applying torque to end 16. Second threaded section 24 should be long enough and of sufficient diameter such that when inserted into a bore formed in phalange P2, the threads 28 grip P2 and do not allow screw 10 to twist. The diameter of second section 22 tapers down from middle section 20 to tip 26. The diameter of first section 12 is preferably constant and may be equal to, less than, or greater than that of middle section 20.

A preferred method of inserting a device according to the invention is to first bend the joint a predetermined angle, then use a K-wire to form the path through the phalanges P2, P3 of the joint into which the device will be positioned. A K-wire or pin is a sterilized, smooth stainless steel pin used in orthopedics and other types of medical applications. It comes in different sizes as needed and provides structure support, and one size has a diameter of about 0.040". A drill with a cannulated tip to receive the K-wire is then used to drill an opening where the K-wire has been positioned. The drill and K-wire are then removed, and a device according to the invention is threaded into the opening. The distal end threads into and is received in P2 and the proximal end in threadingly received in P3.

The bored hole into which the screw 10 fits preferably has an internal diameter that is preferably the size of the screw minus the width of the threads. The pitch and height of the threads of first section 12 are preferably smaller than those of threads 28 in second section 22. In a preferred embodiment, the pitch is 1mm/revolution distal with a smaller pitch in the proximal section. The diameter of the screw maximal is preferably 2.5 mm. The diameter of the screw minor is preferably 1.8 mm. The thread height is preferably about 0.3 mm.

One or more orientation marks may be incorporated into a screw 10 of the present invention. For example, an orientation marker may be placed at or near tip 26, or on central portion 20, allowing the surgeon to know when screw 10 is in the proper position. The orientation marker may be an indentation stamp or may be cast into screw 10 or may be a mark made with a surgical marker.

Having thus described preferred embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A bone fusion screw comprising:
   (a) a first threaded portion having a uniform first diameter, first threads having a first thread pitch and a uniform first thread height, and a driver head; and
   (b) a second threaded portion with second threads having a second thread pitch and a second thread height, wherein the second threaded portion tapers from a second diameter to a smaller, third, diameter, wherein the second thread pitch is greater than the first thread pitch and the second thread height is greater than the first thread height; and (c) a central portion between the first threaded portion and the second threaded portion, wherein the central portion has a uniform diameter.

2. The bone fusion screw of claim 1 that is configured to fuse the DIP joint of a finger.

3. The bone fusion screw of claim 1, wherein the driver head is selected from the group consisting of: a flat screwdriver opening, a Phillips screwdriver opening, a hex head, an Allen wrench head, Torx and Star drive.

4. The bone fusion screw of claim 1, wherein the threads on the second threaded portion are of the same pitch and height.

5. The bone fusion screw of claim 1, wherein the central portion is not threaded.

6. The bone fusion screw of claim 1 that does not include a cannula.

7. The bone fusion screw of claim 1, wherein the first threads have a uniform pitch.

8. The bone fusion screw of claim 1, wherein the second end tapers to a point.

9. The bone fusion screw of claim 1, wherein the central portion is longer than the first threaded portion.

10. The bone fusion screw of claim 1, wherein the central portion and second threaded portion each has a diameter that is less than the diameter of the first threaded portion.

11. The bone fusion screw of claim 1 that further comprises a second end that has a self-tapping feature.

12. The bone fusion screw of claim 1 that is comprised of one of the group consisting of: nitinol, stainless steel, and plastic.

13. The bone fusion screw of claim 1 that includes an orientation marker.

14. The bone fusion screw of claim 13, wherein the orientation marker is one or more of the group consisting of: an indentation stamp, a cast in the screw, and a mark made with a surgical marker.

15. The bone fusion screw of claim 1 that is between ½" and 3" long, or between ¾" and 1¾" long.

16. The bone fusion screw of claim 1 that is between 1 mm to 5 mm in diameter at its thickest point, or about 3 mm in diameter at its thickest point.

17. The bone fusion screw of claim 1, wherein the driver head has a diameter and the first threaded portion has a uniform diameter that is the same as the diameter of the driver head.

18. The bone fusion screw of claim 1, wherein there is a space between the first threads and the driver head.

19. The bone fusion screw of claim 1, wherein the first threads are of the same pitch and height.

20. The bone fusion screw of claim 1 that has a length of between ½" and 2".

21. The bone fusion screw of claim 1 that has a length of between ¾" and 1½".

22. The bone fusion screw of claim 1 that has a maximum diameter of about 2.5 mm to about 3 mm.

23. The bone fusion screw of claim 1, wherein the second thread has a pitch is 1 mm/revolution.

* * * * *